(12) United States Patent
Terashima et al.

(10) Patent No.: US 10,311,969 B2
(45) Date of Patent: *Jun. 4, 2019

(54) MEDICAL MEASURING DEVICE AND MEDICAL MEASURING SYSTEM

(71) Applicant: PHC Holdings Corporation, Minato-ku, Tokyo (JP)

(72) Inventors: Noriyoshi Terashima, Tokyo (JP); Masataka Nadaoka, Ehime (JP); Yoshimasa Oda, Ehime (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/871,021

(22) Filed: Jan. 14, 2018

(65) Prior Publication Data
US 2018/0158540 A1 Jun. 7, 2018

Related U.S. Application Data

(60) Continuation of application No. 15/597,111, filed on May 16, 2017, now Pat. No. 9,904,764, which is a
(Continued)

(30) Foreign Application Priority Data

Dec. 26, 2011 (JP) .................................. 2011-283198

(51) Int. Cl.
*G01N 33/50* (2006.01)
*G16H 10/60* (2018.01)
(Continued)

(52) U.S. Cl.
CPC ........... *G16H 10/60* (2018.01); *A61B 5/0022* (2013.01); *A61B 5/157* (2013.01);
(Continued)

(58) Field of Classification Search
CPC ........ G16H 10/60; G16H 80/00; G01N 33/50; G01N 27/3273; G06F 19/3418;
(Continued)

(56) References Cited

U.S. PATENT DOCUMENTS 5,730,124 A 3/1998 Yamauchi
6,246,966 B1 6/2001 Perry
(Continued)

FOREIGN PATENT DOCUMENTS

CN 102271575 A 12/2011
EP 2374405 A1 10/2011
(Continued)

OTHER PUBLICATIONS

International Search Report of Int'l Appln. No. PCT/JP2012/008308 dated Feb. 26, 2013.
(Continued)

*Primary Examiner* — Samuel P Siefke
(74) *Attorney, Agent, or Firm* — Wenderoth, Lind & Ponack, L.L.P.

(57) ABSTRACT

In a housing configured to mount thereon a biosensor in an attachable and detachable manner in which the biosensor is configured to have a liquid sample of a biological object deposited thereon, the medial measuring device includes a measuring component operable to measure biological information from the liquid sample of the biological object, a recording component operable to store a result measured by the measuring component, and an information protection component operable to determine an access limitation to personal information data stored in the recording component. With this configuration of the device, it is possible to properly protect personal information stored in the device.

4 Claims, 8 Drawing Sheets

Related U.S. Application Data division of application No. 14/367,940, filed as application No. PCT/JP2012/008308 on Dec. 26, 2012, now Pat. No. 9,684,763.

(51) Int. Cl.

| | | |
|---|---|---|
| *A61B 5/00* | (2006.01) | |
| *A61B 5/15* | (2006.01) | |
| *A61B 5/157* | (2006.01) | |
| *G01N 27/327* | (2006.01) | |
| *G06F 19/00* | (2018.01) | |
| *G16H 80/00* | (2018.01) | |
| *A61B 5/145* | (2006.01) | |

(52) U.S. Cl.
CPC .. *A61B 5/150022* (2013.01); *A61B 5/150358* (2013.01); *A61B 5/150862* (2013.01); *G01N 27/3273* (2013.01); *G01N 33/50* (2013.01); *G06F 19/3418* (2013.01); *G16H 80/00* (2018.01); *A61B 5/14532* (2013.01); *A61B 5/6898* (2013.01); *A61B 2560/0266* (2013.01); *A61B 2562/0295* (2013.01)

(58) Field of Classification Search
CPC ........ A61B 5/150862; A61B 5/150358; A61B 5/157; A61B 5/150022; A61B 5/0022; A61B 5/6898; A61B 2562/0295; A61B 2560/0266; A61B 5/14532
See application file for complete search history.

(56) References Cited

U.S. PATENT DOCUMENTS

| | | | |
|---|---|---|---|
| 8,131,478 B2 | 3/2012 | Kai | |
| 8,854,206 B2 | 10/2014 | Kai et al. | |
| 9,904,764 B2* | 2/2018 | Terashima | ............. G16H 80/00 |
| 2004/0046020 A1 | 3/2004 | Andreasson et al. | |
| 2006/0005264 A1 | 1/2006 | Lin et al. | |
| 2007/0023513 A1 | 2/2007 | Andreasson et al. | |
| 2007/0213938 A1 | 9/2007 | Kai | |
| 2008/0083618 A1 | 4/2008 | Neel et al. | |
| 2008/0147044 A1 | 6/2008 | Palmer et al. | |
| 2008/0214919 A1 | 9/2008 | Harmon et al. | |
| 2008/0220814 A1 | 9/2008 | Hedtke et al. | |
| 2009/0239501 A1 | 9/2009 | Matsui et al. | |
| 2009/0264712 A1 | 10/2009 | Baldus et al. | |
| 2010/0179831 A1 | 7/2010 | Brown et al. | |
| 2011/0082711 A1 | 4/2011 | Poeze et al. | |
| 2011/0238324 A1 | 9/2011 | Matsushima et al. | |
| 2012/0004558 A1 | 1/2012 | Uesaka et al. | |
| 2012/0274443 A1 | 11/2012 | Kai et al. | |

FOREIGN PATENT DOCUMENTS

| | | |
|---|---|---|
| EP | 2517620 A1 | 10/2012 |
| JP | H10-323332 A | 12/1998 |
| JP | 2000-222059 A | 8/2000 |
| JP | 2003-288328 A | 10/2003 |
| JP | 2004-097675 A | 4/2004 |
| JP | 2006-270487 A | 10/2006 |
| JP | 2006-301731 A | 11/2006 |
| JP | 2006-302199 A | 11/2006 |
| JP | 2007-193679 A | 8/2007 |
| JP | 2008-043702 A | 2/2008 |
| JP | 2008-214333 A | 9/2008 |
| JP | 2009-000392 A | 1/2009 |
| JP | 2009-232108 A | 10/2009 |
| JP | 2009-544431 | 12/2009 |
| JP | 2010-110380 A | 5/2010 |
| JP | 2010-520724 A | 6/2010 |
| JP | 2010-158352 A | 7/2010 |
| JP | 2011-062472 A | 3/2011 |
| JP | 2011-232789 A | 11/2011 |
| TW | 200601197 A | 1/2006 |
| WO | 95/16970 | 6/1995 |
| WO | 2006/012589 | 2/2006 |
| WO | WO2010/079554 A1 | 7/2010 |
| WO | WO2010/079664 A1 | 7/2010 |

OTHER PUBLICATIONS

European Search Report from the corresponding European Patent Application No. 12861604.2 dated Jun. 1, 2015.

"Access control overview" (2011 Microsoft), updated Jan. 21, 2005; p. 1-2, retrieved from the Internet:URL: https://technet.microsoft.com/en-us/library/cc785144(v=WS.10).aspx [retrieved on May 21, 2015].

Search Report from the corresponding European Patent Application No. 17 158 845.2 dated Jul. 21, 2017.

Office Action dated Sep. 18, 2018 in Chinese Application No. 201610102244.X, with English Translation.

* cited by examiner

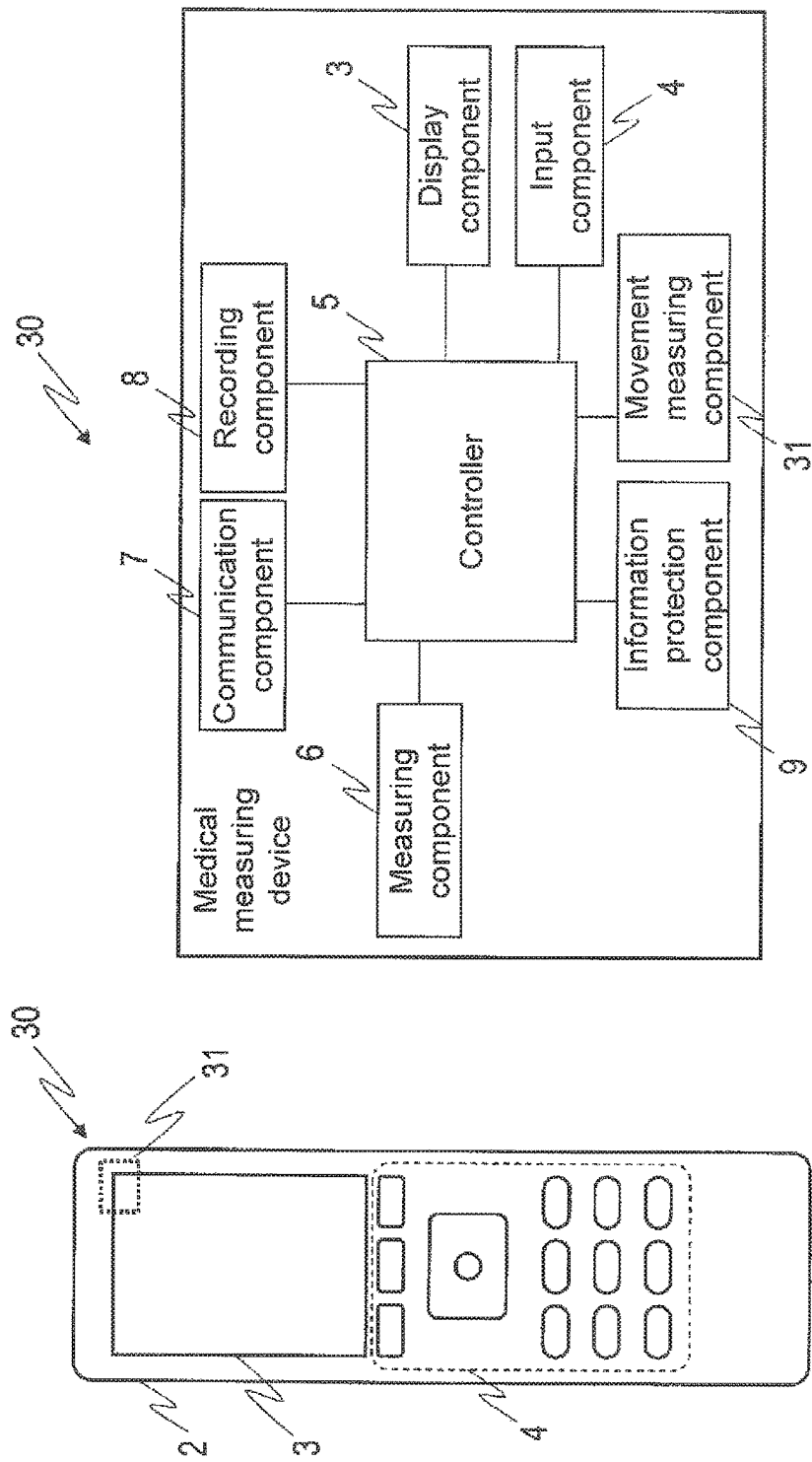

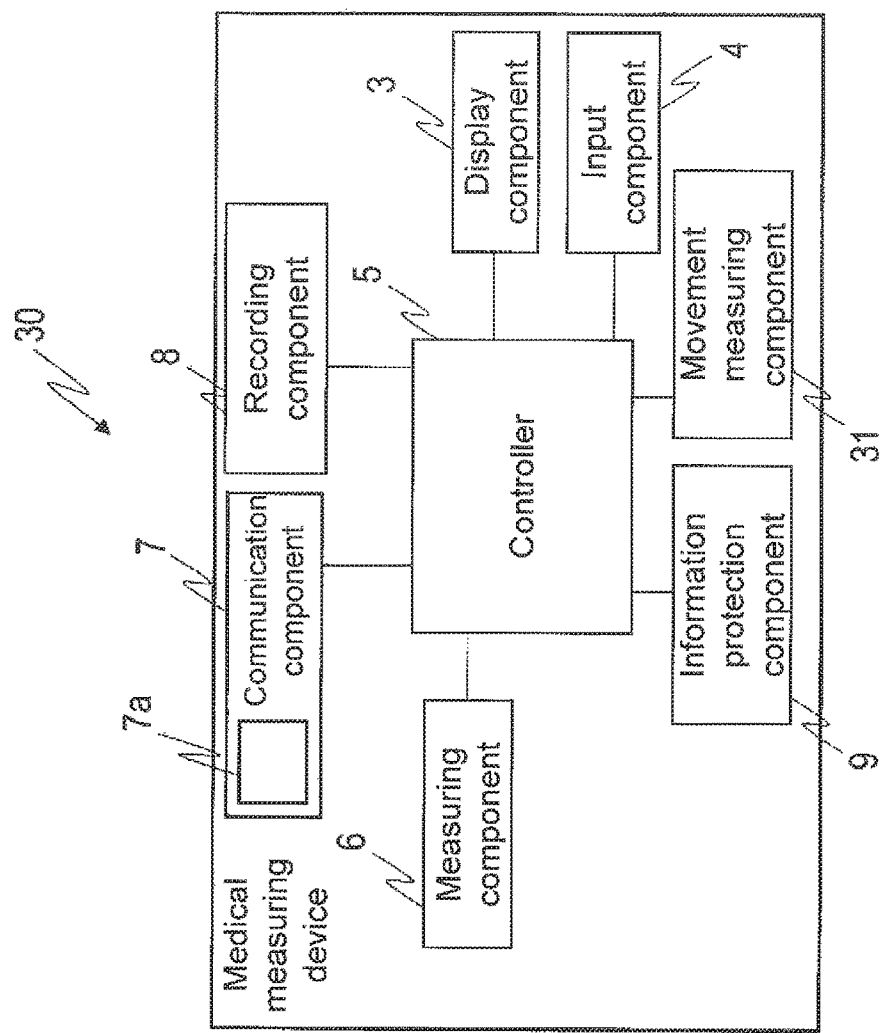
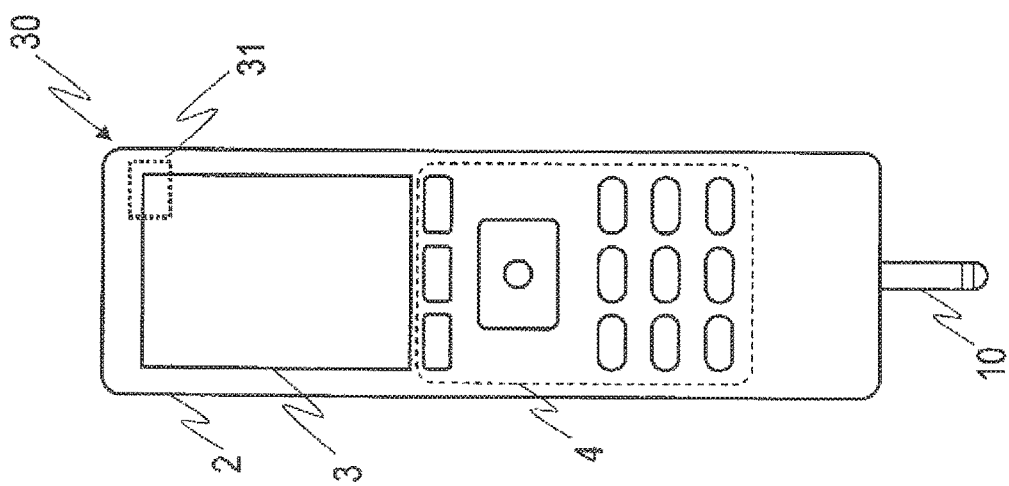
FIG. 5B
FIG. 5A

MEDICAL MEASURING DEVICE AND MEDICAL MEASURING SYSTEM

PRIORITY

This application is a continuation application of and claims priority to U.S. application Ser. No. 15/597,111 filed on May 16, 2017, which is a divisional application of and claims priority to U.S. application Ser. No. 14/367,940 filed on Jun. 23, 2014, which is a National State Application under 35 U.S.C. § 365 of International Application PCT/JP2012/008308 with an international filing date of Dec. 26, 2012, which claims priority to Japanese Patent Application No. JP2011-283198 filed on Dec. 26, 2011. The entire disclosures of U.S. application Ser. No. 15/597,111, U.S. application Ser. No. 14/367,940, International Application PCT/JP2012/008308 and Japanese Patent Application No. JP2011-283198 are hereby incorporated herein by reference.

TECHNICAL FIELD

The present invention relates to a medical measuring device and a medical measuring system for measuring biological information.

BACKGROUND

As a medical measuring device, there is a hand-held type that is easy to carry is mainly used in a medical institution, for example. The medical measuring device is often used in a manner that one device is shared by a plurality of patients. In this case, some medical measuring devices store necessary information specifying at least a patient in the device in order to manage data as a measurement result. The necessary information for specifying a patient is stored in association with the measurement result.

The necessary information for specifying a patient is, for example, a name, a sex, a birth date, etc. of the patient or ID assigned to the patient, which is given from the medical institution. In a case where an ID assigned to the patient is used, the name of the patient, etc. is stored in a management device that communicates with the medical measuring device.

If this type of medical measuring device was taken out by a third person without permission and the data therein was reviewed, there was a possibility that the personal information such as a patient name, etc. stored in the medical measuring device leaks to outsiders.

In order to prevent this, there has been a technology in which a user is not allowed to start using the medical measuring device unless inputting a release code which was set in a management device (see, for example, patent literature 1: Japanese Patent Application Publication No. 2011-062472).

However, in the aforementioned method in which a release code is input, the medical measuring device would significantly deteriorate its user-friendliness. Specifically, in a situation that the user has to take measurements for many patients at a hospital ward or for many outpatients, the measurement efficiency of the device becomes worse because it takes time for the user to input a release code each time the medical measuring device is powered on. As a result, there has been a problem that the user-friendliness of the device deteriorates.

The object is to provide a medical measuring device and a medical measuring system that can suppress deterioration of their user-friendliness and improve a protection performance of personal information.

SUMMARY

A medical measuring device includes a housing configured to mount thereon a biosensor in an attachable and detachable manner, the biosensor being configured to have a liquid sample of a biological object deposited thereon, a measuring component that measures biological information from the liquid sample of the biological object, a recording component that stores a result measured by the measuring component, an information protection component that determines whether or not to prohibit a readout of personal information data stored in the recording component, and a controller that controls a permission or a prohibition of the readout of the personal information data based on a determination result made by the information protection component.

BRIEF DESCRIPTION OF DRAWINGS

FIG. 1A is a diagram showing an external appearance, and FIG. 1B is a block diagram;

FIG. 4 is a diagram showing a configuration of a medical measuring device in the second embodiment, and FIG. 4A is a diagram showing an external appearance, and FIG. 4B is a block diagram;

FIG. 5 is a diagram showing a configuration of a medical measuring device in the third embodiment, and FIG. 5A is a diagram showing an external appearance, and FIG. 5B is a block diagram;

DETAILED DESCRIPTION

Hereinafter, embodiments of the medical measurement device of the present invention will be described with reference to the drawings in detail.

(First Embodiment)

In the present embodiment, it will be described in a case that the medical measuring device is used in a hospital as an example of the use.

Figure 1:
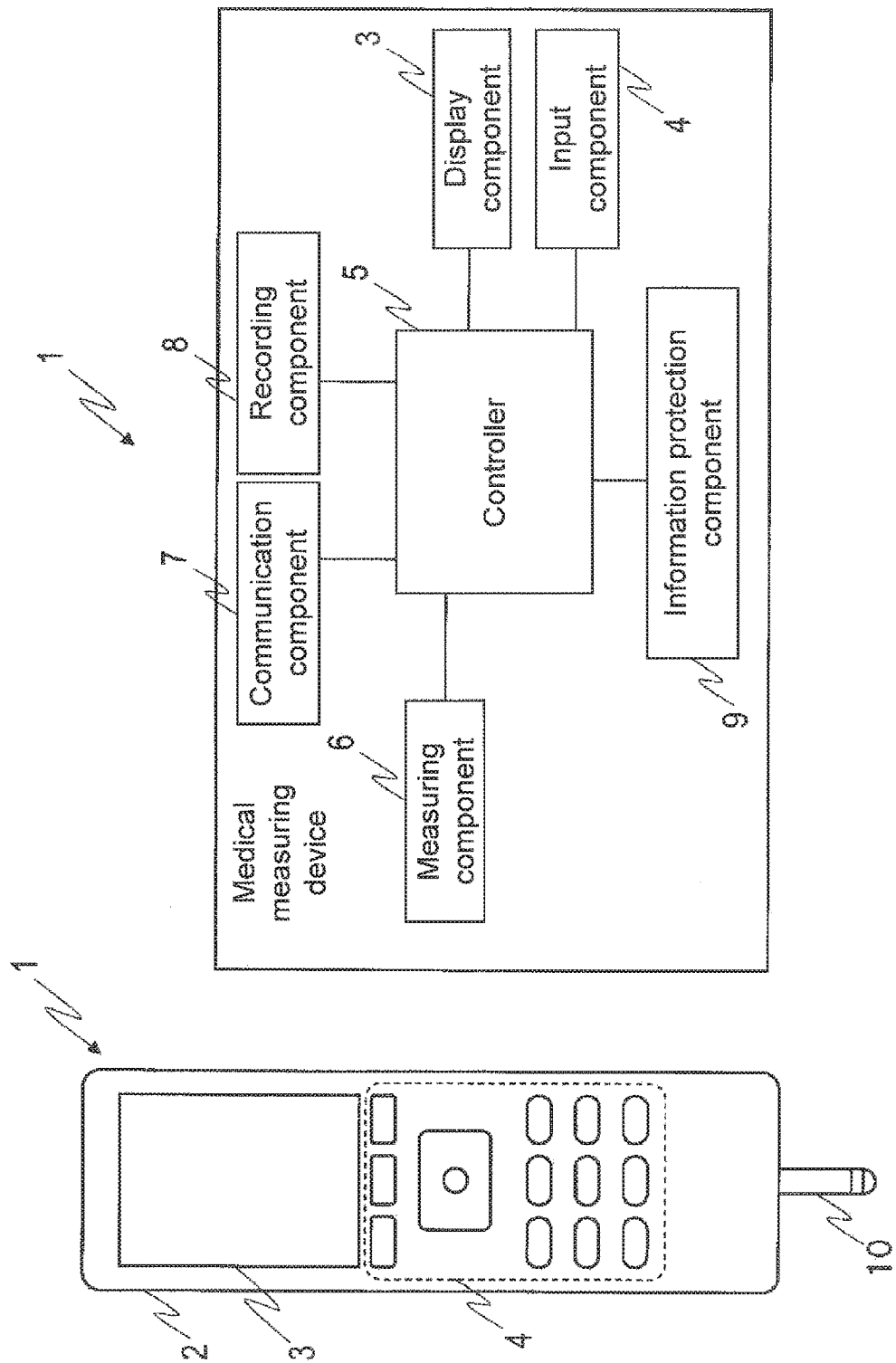
FIG. 1 is a diagram showing a configuration of a medical measuring device in the first embodiment.

FIG. 1 is a diagram showing a configuration of a medical measuring device 1. FIG. 1A is a diagram showing an external appearance of the medical measuring device 1. FIG. 1B is a block diagram of the medical measuring device 1. As shown in FIG. 1, the medical measuring device 1 is a hand-held type measuring device. The medical measuring device 1 is comprised by a device main body (housing) 2, a display component 3, and an input component 4. In the medical measuring device 1, a disposable biosensor 10 is detachably attached in the device main body 2. A liquid sample of a biological object is deposited onto the biosensor 10. Further, the device main body 2 is formed in a compact shape so that a nurse or a patient who is the user can hold it by one hand.

As shown in FIG. 1B, the medical measuring device 1 is provided with a device main body 2, a display component 3, an input part 4, a controller 5, a measuring component 6, a communication component 7, a recording component 8, and an information protection component 9.

The display part 3 is operated according to an instruction received from the controller 5. The display part 3 displays a level of glucose concentration measured by the measuring component 6 as biological information. Further, the display part 3 displays various kinds of information for the user.

The input component 4 is a device to receive an input of an operation instruction, an identification number, etc. For example, the input component 4 is a button provided on the device main body 2. Alternatively, the input component 4 is an optical reading device such as a barcode reader. Alternatively, the input component 4 may be a near field communication terminal such as an RF-ID system or may be a device that performs an input a sound recognition. The input component 4 of the present embodiment is equipped with a combination of a plurality of input devices. Further, information inputted by the input component 4 is transmitted to the controller 5, The controller 5 controls the medical measuring device 1 entirely. Information is inputted into the controller 5 from the input component 4, the measuring component 6, and the information protection component 9. The controller 5 gives instructions to the display component 3, the communication component 7, and the recording component 8 based on the inputted information. The controller 5 is comprised by a program memory that stores programs, which were designed so as to control the medical measuring device 1 entirely, and a microcomputer that executes the programs.

The measuring component 6 receives an instruction from the controller 5 and measures biological information from a liquid sample of the biological object deposited on the biosensor 10. Therefore, the measuring component 6 has a configuration to include a sensor mounting component (not shown in the drawing) having a connector which is electrically connected with an electrode of the biosensor 10 when the biosensor 10 is inserted into the device main body 2. The measuring component 6 applies a voltage or an electric current to each electrode of the biosensor 10 through the connector when the liquid sample is deposited onto the biosensor 10. The measuring component 6 measures biological information in the liquid sample based on the values of the electric current or the voltage obtained in response to the application of the voltage or the electronic current. In the present embodiment, the biological information of the liquid sample of the biological object denotes a glucose concentration level in blood sampled from a human body. An electrochemical measurement method for measuring a glucose concentration in blood is explained as an example.

The communication component 7 receives an instruction from the controller 5 and performs a transmission or a reception of data with other devices such as a server, a personal computer, etc. through communication lines. For example, the communication component 7 transmits a glucose concentration level measured by the measuring component 6 or an identification number inputted to the input component 4 to other devices. Further, the communication component 7 receives a list of identification numbers from other devices. The communication component 7 incudes a wired or wireless interface for connecting with other devices. For example, when a wired connection is used, it is a connector to install a connection cable. Further, when a wireless connection is used, it is an antenna for transmitting or receiving a wireless radio wave.

The recording component 8 stores personal information data. The recording component 8 has at least a patient information area and a device information area. In the patient information area, the patient information data related to each patient is stored. In the device information area, the device information data related to the medical measuring device 1 is stored. In the present embodiment, the data stored in the patient information area and the device information area are related to directly or indirectly personal information. Accordingly, the combination of the both information is called as personal information data. That is, depending on a disclosure regulation signal of the information protection component 9, the personal information data is prohibited from being read from the recording component 8. In the present embodiment, not only the readout of the personal information data is prohibited, but also, the writing of the personal information to the recording component 8 may be prohibited.

In the patient information area of the recording component 8, at least a result measured by the measuring component 6 is stored. Further, the recording component 8 receives and stores the measurement result that the measuring component 6 outputs, the information that is input by the input component 4, and the information that the communication component 7 receives, etc. through the controller 5. The reproduction and recording of the data to the recording component 8 is controlled by the controller 5.

The information protection component 9 determines whether or not the readout of the personal information data stored in the recording component 8 is prohibited. This personal information data includes at least the measurement result output by the measuring component 6 and is the data related to personal information. Therefore, the information protection component 9 functions to protect the personal information data stored in the device main body 2, specifically, in the recording component 8. Because of this, in a case of detecting an occurrence of a specific condition, the information protection component 9 outputs a disclosure regulation signal, which orders not to disclose the personal information data, to the controller 5. Accordingly, the controller 5 controls a permission or a prohibition of the readout of the personal information data based on the determination result of the information protection component 9.

Figure 2:
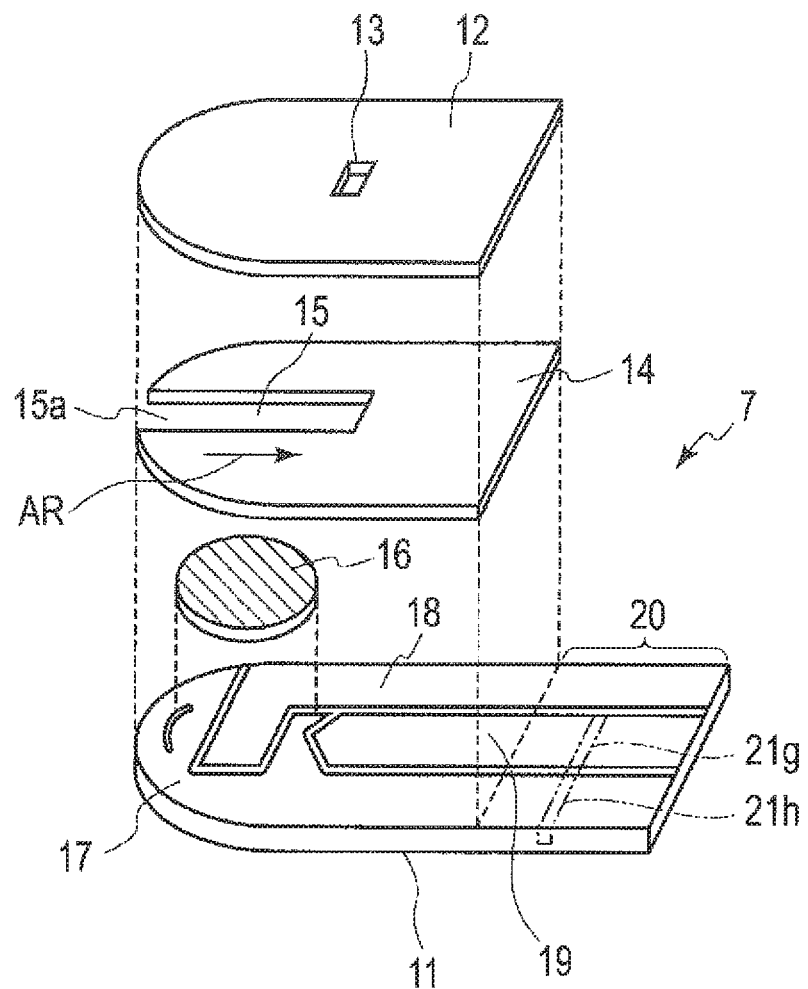
FIG. 2 is an exploded diagrammatic view of a biosensor.

Next, a disposable biosensor 10 that is inserted into the medical measuring device will be explained in reference to FIG. 2. FIG. 2 is an exploded diagrammatic view of the biosensor 10 that is inserted into the medical measuring device 1.

The biosensor 10 includes an insulated substrate (hereinafter referred to as simply "substrate 11") made of polyethylene terephthalate, etc. The surface of the substrate 11 is formed with a conductive layer. For example, the conductive layer is made by a noble metal such as gold or palladium, etc. or an electrically conductive substance such as carbon, etc. The conductive layer is formed on the substrate 11 by the screen printing method or the sputtering vapor deposition method. The conductive layer may be formed on an entire surface of the substrate 11, or may be formed on at least a part of the substrate 11. Further, the biosensor 10 includes an insulated substrate 12 on its top surface. An air hole 13 is provided on a central part of the substrate 12. A spacer 14 having a notch part is sandwiched between the substrate 11 and the substrate 12. The biosensor 10 is integrally configured with the substrate 11, the spacer 14 and the substrate 12.

On the substrate 11, a counter electrode 17, a measurement electrode 18, and a detection electrode 19 are formed by the conductive layer which is divided by a slit. Each of the electrodes 17, 18, 19 may be formed in at least a part of the substrate 11. Further, each of the electrodes 17, 18, 19 may be connected to the medical measuring device 1 by a lead wire in a state where the biosensor 10 is inserted into the device main body 2.

The spacer 14 is arranged so as to cover the counter electrode 17, the measurement electrode 18 and the detection electrode 19 on the substrate 11. A sample supply path 15 is configured by a rectangular shaped notch part provided in the center of a front edge part of the spacer 14. Further, blood is deposited on a sample deposition component 15a which is at the front edge of the sample supply path 15. When blood is deposited on the sample deposition component 15a, the blood is pulled toward the air hole 13 of the substrate 12 (in the direction of an arrow AR in FIG. 2.) by the capillary action.

The sample layer 16 has such a shape and dimension that cover the counter electrode 17, which is exposed through the notch part of the spacer 14, the measurement electrode 18, and the detection electrode 19.

An oxidation reduction enzyme and an electron acceptor are included in the sample layer 16. The oxidation reduction enzyme and the electron acceptor are dissolved in and reacted with the blood suctioned in the sample supply path 15. After the reaction has been completed, the medical measuring device 1 electrochemically oxidizes the reduced electron acceptor. The medical measuring device 1 measures the glucose concentration of the blood based on the electric current obtained by the oxidation. These series of reactions are read according to electric current generated due to an electrochemical change, using the counter electrode 17, the measurement electrode 18 and the detection electrode 19.

Further, an identification component 20 is a member that identifies the type of the biosensor 10 and the difference in output characteristics in each manufacturing lot for each device main body 2. A part corresponding to the identification component 20 of the counter electrode 17 and the detection electrode 19 is formed with a combination of a slit 21g and a slit 21h. Therefore, the device main body 2 can identify the difference of the electrical output characteristic of each biosensor 10.

On the substrate 11 of the biosensor 10, the counter electrode 17, the measurement electrode 18, the counter electrode 17, and the detection electrode 19 from the sample deposition component 15a are formed in that order along the flow direction (arrow AR) of the blood. The arrangement of the counter electrode 17 and the measurement electrode 18 may be interchanged.

Further, a predetermined distance is provided between the measurement electrode 18 and the detection electrode 19 along the flow direction of blood. Therefore, whether or not a sufficient amount of blood is surely absorbed can be determined by the detection electrode 19.

When the user starts measuring by using the medical measuring device 1 and the biosensor 10 as described above, first, the user inputs the ID of the user (nurse), who is a measurer, the ID of the patient, who is a person to be measured, and the ID of the biosensor by using the input component 4. As an example of this inputting, the user may input the ID by pushing a button of the input component 4. When a barcode reader is provided to the input component 4, the user may input the ID by having the barcode reader read a barcode which is tagged on each of the device and biosensor. When the RF-ID system is provided to the input component 4, the user may input the ID by having the ID read from a RF-ID tag which is tagged on each of the device and biosensor. When the inputs of the ID were completed, the preparation before measurement is completed.

When the preparation of the measurement has been completed, next, the user inserts the biosensor 10. When the biosensor 10 has been inserted into the sensor mounting component, the insertion is detected by the measuring component 6 and is transmitted to the controller 5. The controller 5 instructs the measuring component 6 to start measurement.

The measuring component 6 that have received an instruction from the controller 5 to start measurement starts applying a voltage to the counter electrode 17, the measurement electrode 18, and the detection electrode 19 of the biosensor 10 through the connector. At this time, blood is not deposited on the sample deposition component 15a of the biosensor 10 yet.

When blood is deposited on the sample deposition component 15a by the user, the blood is pulled in the sample supply path 15 by the capillary action and is spread out in the direction of the air opening 13. When the spread blood is reached to an electrode which is either one of the counter electrode 17, the measurement electrode 18 or the detection electrode 19 arranged on the side closest to the sample deposition component 15a, the measuring component 6 can detect the deposition of blood by a change of response characteristics of the voltage obtained through the connector After a specific time from the deposition of blood has passed, or when a change of response characteristics of another voltage in the counter electrode 17, the measurement electrode 18 and the detection electrode 19 has occurred, the measuring component 6 starts measuring a level of glucose concentration in the blood.

After the measurement has started, the measuring component 6 applies a voltage to the plurality of electrodes at least one time. The measuring component 6 acquires at least one response value of electric current generated due to an electrochemical change during the application of voltage and stores it as an electric current profile. The measuring component 6 determines a glucose concentration level by applying a Cottrell method or other algorithm to the stored electric current profile and outputs it to the controller 5 as the measurement result.

The controller 5 instructs the display component 3 to display a value of the measured glucose concentration thereon. At the same time, the controller 5 displays candidates of information to be associated with the measured glucose concentration level and the user can select from among the candidates by using the input component 4. Here, the candidates of information are information related to, for example, meal such as before meal, after meal, etc. and using the candidates of information, the user can see the state at the time of measurement when the user checks the measurement result of glucose concentration level later. The user can separately set what kind of candidates is selectable. Further, not only the user selects from among the candidates of information, but also the user may input any characters by using the input component 4.

When the inputting has been completed by the user, the controller 5 records to the recording component 8 a batch of data that includes the ID of the measurer, the ID of the person who undergoes the measurement, the ID of the biosensor 10, the measurement result of glucose concentration, and the related information specified by the user.

Hereinafter, the batch of data is referred to as measurement managing data. The measurement managing data includes the patient information data and is stored in the patient information area.

Further, the controller 5 monitors a value of the measured glucose concentration. In a case where the measured glucose concentration level is an unexpected value which can not be obtained in a normal measurement, or when the value is out of the range that is designated by the user, the controller 5 adds an unexpected value flag, which indicates the abnormality, in the measurement managing data. When the controller 5 adds the unexpected value flag, a detection of the unexpected value is indicated by a display of the display component 3 and is notified to the user.

The above measurement is repeated, and then, a plurality of measurement managing data for a plurality of patients is stored in the recording component 8 and also the measurement results of glucose concentration of the respective patients are stored.

The controller 5 controls the display component 3 so as to display the stored measurement results of glucose concentration in a format designated by the user. For example, the display component 3 displays values of the measurement results for only the date of the measurements designated by the user. Alternatively, the display component 3 may display a list or a graph of a plurality of past measurement results so that the user can check, for example, a trend in the changes of glucose concentration levels for the person who undergoes the measurement (patient).

In a case that the measurement results of glucose concentration are displayed, the user designates an object or a format of display by using the input component 4, and then, the controller 5 reads the stored measurement managing data in the recording component 8 and retrieves the information that is necessary for the display. The retrieved information is then processed if necessary and is displayed on the display component 3.

When the user selects the measurement result of a specific patient among the measurement results of the plurality of patients stored in the recording component 8, it is difficult for the user to confirm whether or not the patient is properly selected with only the patient ID. That is, even when alphabets and numbers are displayed on the display component 3 as the patient ID, it is difficult for the user to determine whether or not the desired patient is selected. Accordingly, there may be a possibility of erroneous display that causes a wrong patient to be selected.

Therefore, the medical measuring device 1 is desired to display not only the patient ID but also a plurality of personal information such as name, sex, birth date, etc. of the patient so that an erroneous display is prevented. Accordingly, the information specifying an individual such as name, sex, birth date, etc. of the patient and a patient table that indicates a correspondence between the information specifying the individual and the patient ID are recorded in the patient information area of the recording component 8.

The user may determine whether the information such as name of the patient, etc. is displayed on the display component 3. The controller 5 reads the information designated by the user from the patient information area of the recording component 8.

One of the methods for storing patient information data as the personal information of patients in the patient information area of the recording component 8 is that the user directly inputs it by using the input component 4. That is, the user may manually input the personal information of each patient with respect to each patient ID.

The other method is to read another database. For example, in such an environment such as hospital where many patients undergo the measurement, it is very inefficient for the user to directly input the information of patient for each patient. Therefore, a unified patient database such as an electronic medical chart, etc. is read and the personal information of patient is replicated in the recording component 8. The patient database is stored and managed in the server provided in, for example, a hospital.

Therefore, the controller 5 accesses to the patient database in the server when the communication component 7 established a communication with the server in the hospital. The controller 5 acquires the personal information of patient from the server and stores the replicated data in the patient information area of the recording component 8.

The information protection component 9 determines whether or not the medical measuring device 1 is used in a secure and favorable situation based on the conditions described later. When a determination was made that the medical measuring device 1 is not in a favorable situation, the information protection component 9 outputs to the controller 5 a disclosure regulation signal for regulating a disclosure of at least personal information or information related to such personal information.

When the disclosure regulation signal is output from the information protection component 9, the controller 5 stops a readout of the personal information data. Specifically, the readout of the personal information data including data from the patient information area of the recording component 8 is prohibited while the disclosure regulation signal is output. When the readout has been requested by the user, the controller 5 outputs to the display component 3 a notification that the readout of the personal information data is prohibited. That is, the user cannot read out the personal information data including data from the patient information area of the recording component 8. In other words, the personal information is locked.

Such processes performed by the controller 5 and the information protection component 9 as to whether or not the personal information data is locked are always performed except when the power of the medical measuring device 1 is turned off.

Therefore, when the medical measuring device 1 is used in a favorable situation, the stored personal information data can be freely read out so that it improves usability of the device, but when it is not in a favorable situation, the stored personal information data is prohibited from being disclosed.

Here, the favorable situation and unfavorable situation are related to the protection of the personal information data. Specifically, the favorable situation means that employees such as nurses, etc. in a hospital perform measurements for patients, reading the measurement results, and using the measurement results for an examination or a treatment in a hospital ward or a hospital out-patient. That is, the "favorable situation" is a condition that the medical measuring device 1 is favorably used for protection of the personal information data. The "unfavorable situation" is a case that a third person who is not an employee of the hospital takes the medical measuring device 1 out of the hospital for a purpose other than the measurements, and reviews and gets the personal information data stored in it. That is, the "unfavorable situation" is a condition that the medical measuring device 1 is not favorably used for protection of the personal information data.

However, when the medical measuring device 1 is simply used as a measuring device, the users always want to use the medical measuring device for only the purpose of glucose concentration measurement, no matter what conditions the medical measuring device is used in. Therefore, the controller 5 validates only the measurement operation in the measuring component 6 even while the disclosure regulation signal is output from the information protection component 9. The controller 5 records the measurement result measured by the measuring component 6 in association with a measurement date in the recording component 8. The controller 5 controls the display component 3 so as to display the measurement result thereon. Even in this case, the readout of the personal information data including data from the patient information area is prohibited and the readout of the personal information data is locked.

Therefore, an auxiliary area that records the measurement results obtained while the disclosure regulation signal is output is provided separately from the patient information area that records the aforementioned normal measurement managing data in the recording component 8. When the instruction for reading the measurement results is input through the input component 4 by the user while the disclosure regulation signal is output, the controller 5 allows the display component 3 to display only the measurement data recorded in the auxiliary area.

A screen of the user interface displayed on the display component 3 may be a simple menu by the controller 5 while the disclosure regulation signal is output from the information protection component 9. The simple menu denotes a menu that does not display items for the readout of the personal information data including data from the patient information area. On the other hand, the full menu denotes a normal menu that displays all items for the readout of the personal information data. That is, the simple menu is a menu that limits a part of the functions related to the personal information data. The full menu is a menu that is available for all functions including the functions related to the personal information data. Both of the programs for the full menu and the programs for the simple menu are preliminarily stored in the program memory in the controller 5. The controller 5 switches between the full menu and the simple menu by executing the programs according to whether the disclosure regulation signal is output or not.

In the simple menu, at least an items for instructing an execution of measurement and an item for displaying a measurement result may be displayed. Alternatively, only the item for displaying a measurement result may be displayed. In this case, when it is detected that the biosensor 10 has been inserted in the sensor mounting component provided in the device main body 2, the controller 5 instructs the measuring component 6 to start a measurement.

Therefore, it is possible to perform a measurement of glucose concentration even outside the hospital. For example, there is a case that needs to measure a glucose concentration, when, for example, a patient needs to be transferred to the outside of a hospital and a follow-up examination needs to be performed during the transfer. In this case, the nurses can use the medical measuring device 1 for patients in a hospital ward or a hospital out-patient and take out the device for accompanying the patients. This results in saving time to prepare a separate measuring device.

Next, the aforementioned determination processes in the information protection component 9 as to whether the medical measuring device 1 is used in a favorable situation or unfavorable situation will be explained. More specifically, the information protection component 9 determines whether or not the medical measuring device 1 is used in a hospital or outside hospital.

Figure 3:
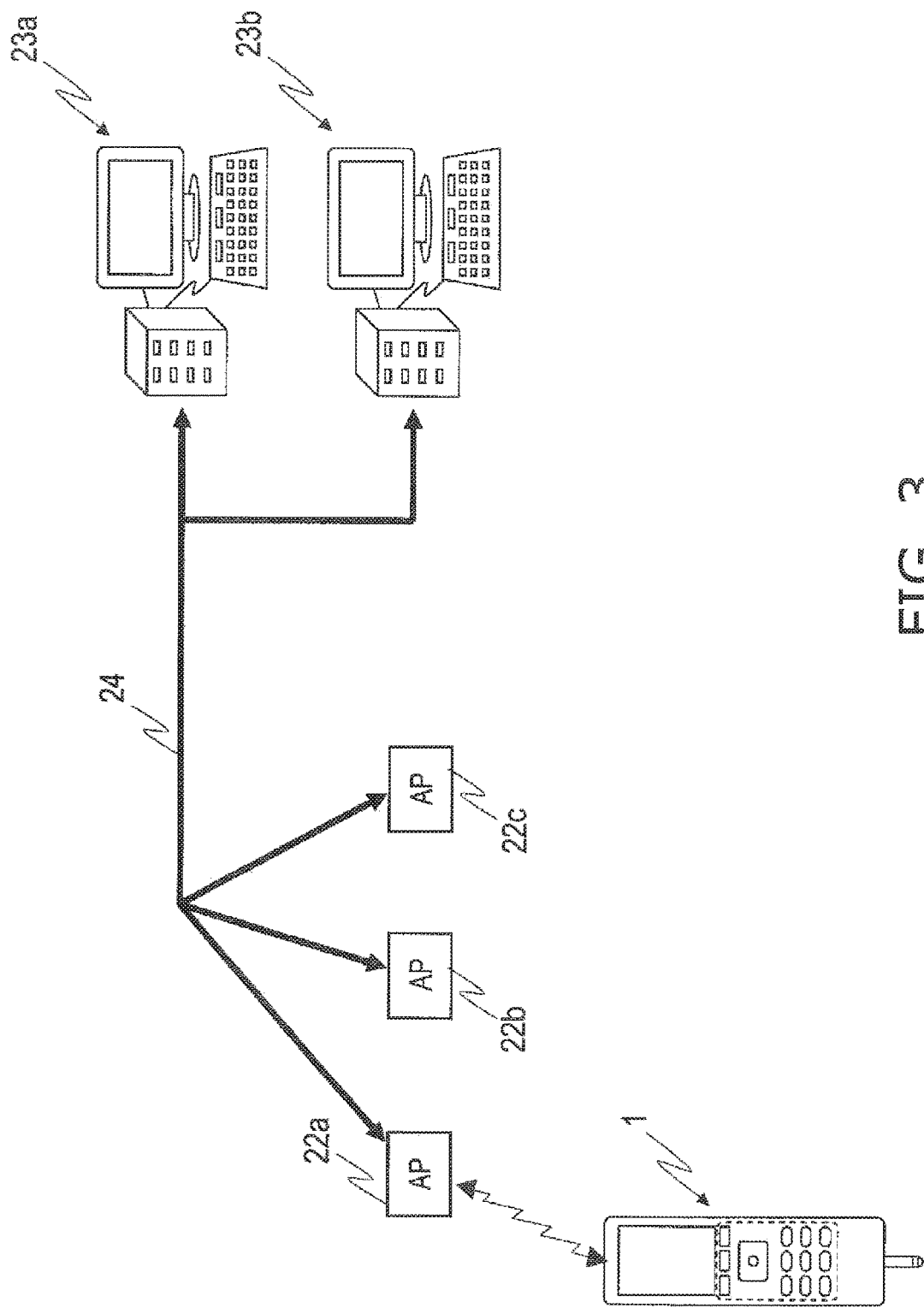
FIG. 3 is a schematic diagram showing a configuration of network in which the medical measuring device is connected.

First, in the present embodiment, the favorable situation that the medical measuring device 1 is used will be explained in reference to FIG. 3. FIG. 3 shows a situation that the medical measuring device 1 connects to a wireless network environment inside hospital. Access points 22*a* to 22*c* as an external device (abbreviation as AP in the drawing, and hereinafter referred to as collectively "access point 22") are a plurality of wireless access points installed indoors or not within the grounds of the hospital. That is, the access points 22 are arranged in a facility where the personal information data recorded in the medical measuring device 1 is allowed to be read out, and it is possible for the access points 22 to communicate with the medical measuring device 1 that permits the readout of the personal information data. These access points 22 are appropriately provided in sufficient numbers and arrangements so as to enable the medical measuring device 1 to perform a wireless communication in all the places within the grounds of the hospital. The servers 23*a*, 23*b* (hereinafter referred to as "server 23") are provided in the hospital and they are the computer that manages the patient database. The access points 22*a* to 22*c* and the servers 23*a*, 23*b* are connected by a wired or wireless intranet 24. In the present embodiment, the communication component 7 of the medical measuring device 1 performs a wireless communication with the access points 22. The communication component 7 performs a wireless communication on a regular basis by connecting with any of the access points 22*a* to 22*c* that is within the area of the wireless communication while the medical measuring device 1 is turned ON. The communication component 7 selects one of the plurality of access points 22*a* to 22*c* and connects with it when any of the plurality of access points 22*a*. to 22*c* is connectable for communication. Normally, each of the access points 22*a* to 22*c* is provided with a specific number, which is generally called as an address. When the communication component 7 establishes a communication with one of the access points 22*a* to 22*c*, the communication component 7 receives an address of the communicating access point 22 and outputs it to the controller 5.

The controller 5 reads out a plurality of addresses, which has already been registered and recorded in the recording component 8 when the communication component 7 receives an address of the access point 22 by connecting with the access point 22. The plurality of registered addresses is preliminarily stored in the device information area of the recording component 8. The information protection component 9 receives the address, which was received by the communication component 7, from the controller 5, and the plurality of registered addresses is read out from the recording component 8. The information protection component 9 checks whether or not the received address corresponds to any of the plurality of registered addresses and when it corresponds, the determination is made that the medical measuring device 1 has established an available wireless communication. That is, it determines that the medical measuring device 1 is located within the grounds of the hospital, and it is used in a favorable situation.

The plurality of registered addresses is preliminarily registered in the medical measuring device 1. Specifically, an initial setting is performed and the addresses of the access points 22*a* to 22*c* are obtained at the time when the medical measuring device 1 is installed in a facility for the first time. The addresses may be obtained by performing a connection test of a communication with the access points 22a to 22c, respectively. Further, when there are many access points 22, the database for the addresses may be prepared in any of the servers 23a, 23b, or a terminal for maintenance, from which the addresses are obtained.

The initial setting may be prohibited from being executed by a person other than a manager or a person in charge of the maintenance in a facility so that it can prevents a third person from additionally registering an unauthorized address of the access points 22.

On the other hand, when the communication component 7 cannot be connected to any of the access points 22a to 22c for a communication, or when an address of the connected access point 22 does not correspond to any of the plurality of registered addresses stored in the recording component 8, the information protection component 9 determines that it is used in an unfavorable situation. This implies that there is no access point 22 managed in a facility, or that the medical measuring device 1 is used outside the hospital. At this time, the information protection component 9 outputs a disclosure regulation signal to the controller 5. When the disclosure regulation signal is inputted, the controller 5 locks the readout of the personal information data in the recording component 8 and its notification is made on the display component 3.

The medical measuring device 1 is portable so that it is sometimes moved beyond the wireless communication area in which one access point 22 is connectable for communication. Therefore, in a similar manner as a mobile radio communication, the communication component 7 searches a connectable access point 22 at a moving destination so as to freely switch to an access point which becomes the other end of the communication. In this case, the communication component 7 receives an address of an access point every time the access point is switched and a communication is reconnected to the new access point, and it checks whether or not an address corresponds to any of the registered addresses.

In this case, as a result of the access point 22 moving beyond its effective communication range, when a wireless communication cannot be established, or when an access point having an address, which is not registered, is connected for a communication, the information protection component 9 may immediately output a disclosure regulation signal to the controller 5. Further, the information protection component 9 may output a disclosure regulation signal to the controller 5 after a predetermined time has elapsed since the time that the wireless communication with a registered access point was disconnected.

That is, as a simplest formation, in a case that the medical measuring device 1 is turned on or it is taken out, or in a case that it is instructed by the user, etc. the medical measuring device 1 performs an operation to connect with an access point 22 for a wireless communication. The determination whether it is used in a favorable situation or an unfavorable situation is made by the information protection component 9 depending on whether or not the communication component 7 can be connected with a specific access point 22, which was preliminarily specified, for a communication.

The communication component 7 may have a function to measure an intensity of a wireless communication radio wave. The communication component 7 outputs the intensity of the received radio wave as reception radio wave intensity to the controller 5. A correspondence relation between an address of the connected access point 22 and a range of the reception radio wave intensity is preliminarily recorded in the recording component 8. The information protection component 9 checks whether or not the reception radio wave intensity of the communication component 7 is within the allowable range recorded in the recording component 8, and when it is out of the allowable range, a disclosure regulation signal is output to the controller 5.

Generally, the radio wave intensity attenuates due to a shielding material such as a wall. Accordingly, by setting a lower limit of the reception radio wave intensity, the information protection component 9 can determine whether it is used in a favorable situation or an unfavorable situation based on whether there is a shielding material between an access point and a medical measuring device.

Further, the radio wave intensity is generally attenuated in proportion to the distance from a radio wave radiation source. Accordingly, by setting a lower limit of the reception radio wave intensity, the information protection component 9 can determine whether it is used in a favorable situation or an unfavorable situation based on a distance from an access point.

Accordingly, even when the medical measuring device 1 is used in a facility of a hospital but in a specific area surrounded by a shielding material such as a waiting room where unspecified persons go in and out, it is possible to prohibit the medical measuring device 1 from reading the personal information data. Further, even when an installed access point 22 provides a wide effective communication range and is able to perform a communication in a specific area outside the hospital, it is possible that the medical measuring device 1 is allowed to read out the personal information data only within the grounds of the hospital.

The medical measuring device of the present embodiment as described above determines whether or not the personal information data is disclosed after checking the other end of a wireless communication. Therefore, while the usability of the device is not deteriorated, the protection performance of the personal information data can be improved.

In the present embodiment, the controller 5 may prohibit the readout of only the patient information area of the recording component 8 while a disclosure regulation signal is output from the information protection component 9. Further, in addition to the patient information area, the controller 5 may prohibit the readout of the device information area in the recording component 8.

In the device information area, the necessary data for establishing a communication with the server 23 by connecting with an access point 22 is stored in the medical measuring device 1. Specifically, the network setting data such as a device ID of the medical measuring device 1 itself, an IP address, etc., an address of the access point 22, an IP address of the server 23, etc. are stored in the device information area. If a third person reads the data, there is a possibility that the third person sets necessary data for a communication in a medical measuring device other than the medical measuring device 1 to imitate the medical measuring device 1. In this case, there is a possibility that the imitated device reads the patient database stored in the server 23 by connecting and communicating to the server 23 without authorization. Therefore, by prohibiting the readout from the device information area, the medical measuring device 1 can improve the protection performance of the personal information data against the unauthorized access by a third person.

In the present embodiment, the controller 5 prohibits the readout of the patient information area in the recording component 8 when a disclosure regulation signal is output from the information protection component 9. However, when a disclosure regulation signal is output, the controller 5 may delete all the patient information data in the patient information area.

With this operation, even when a third person takes out the medical measuring device 1 and a disclosure regulation signal is output to the controller 5 from the information protection component 9, the patient information data is not existed anymore in the medical measuring device 1. Because of this, it is possible that the medical measuring device 1 further improves the protection performance of the personal information data.

In a case that the patient information data is deleted, when the medical measuring device 1 is used in a favorable situation again and is connected for a communication in a hospital, it is preferable that the medical measuring device 1 accesses the patient database in the server 23 and obtains the patient information data and store it to the patient information area in the recording component 8.

In the present embodiment, even when the medical measuring device 1 is used in an unfavorable situation such that the readout of the personal information data is locked, only the measurement of glucose concentration can be performed, but it is not limited to this. For example, when the medical measuring device 1 is taken out in an unfavorable situation, that is, a disclosure regulation signal is output from the information protection component 9, the controller 5 may stop almost all of its functions so that the measurement of glucose concentration cannot be performed and the measurement results cannot be reviewed. In this case, the controller 5 may control the display component 3 so as to display contact information of a department, which keeps the medical measuring device 1, or a request for returning the device to the department.

In the present embodiment, an example in which the medical measuring device 1 is used in a hospital was disclosed, but it is not limited to this. It can be widely used in a situation where many persons undergo the measurement and the measurement results are managed, such as other medical institutions, research facilities, company's business facilities, etc.

Alternatively, it is possible to apply for a personal use. With a configuration that a wireless access point is provided in a home of the user and it is connected to a home server in the home or a server of a medical institution, etc. through the Internet, even when the medical measuring device 1 is taken out from the home, it is possible to improve the protection performance of the personal information data of the user.

(Second Embodiment)

Next, a medical measuring device 30 will be described as the second embodiment of the present invention. The medical measuring device 30 shown as the present embodiment includes another determination processing to prohibit the information protection component 9 from reading out the personal information data. The medical measuring device 30 shown as the second embodiment is configured as shown in FIG. 4. FIG. 4A shows a concept of an arrangement of a movement measuring component in the medical measuring device 30, and FIG. 4B) shows a block diagram of the medical measuring device 30.

As shown in FIG. 4, in the present embodiment, inside of the device main body 2 of the medical measuring device 30, a movement measuring component 31 is provided to detect a movement of the device main body 2. The movement measuring component 31 is configured by a combination of an acceleration sensor and a gyro sensor. The movement measuring component 31 detects a moving amount and a tilting amount in three axes of X-axis (longer direction), Y-axis (shorter direction), and Z-axis (height direction) of the device main body 2. As far as the movement measuring component 31 can detect a moving amount and a tilting amount of three axes of the device main body 2, the movement measuring component 31 may be formed by one sensor. Hereinafter, the moving amount and the tilting amount detected by the movement measuring component 31 are collectively referred to as a movement amount.

The movement measuring component 31 is provided to support a situation determination based on a connection with the access point 22 in the first embodiment. In order for the device to determine whether or not the medical measuring device 30 exists in a facility of a hospital, it is preferable that the access points 22 are arranged all over the facility of the hospital place such that it is possible to establish a communication with an access point 22 anywhere in the facility. However, when the access points 22 are not arranged all over the facility, there is a blank area where the wireless communication between the access point 22 and the medical measuring device 30 can not be established. In such a blank area, some kind of countermeasure is further required to be taken, in addition to the method shown in the first embodiment.

In the second embodiment, the medical measuring device 30 estimates a moving amount of the medical measuring device 30 based on the results measured by the movement measuring component 31. By using the moving amount, in a specific distance outside of the effective wireless communication range of the access point 22, the information protection component 9 can determine that the medical measuring device 30 is used in a favorable situation. Here, the effective wireless communication range of the access point 22 is a range that the intensity of wireless radio wave radiated from the access point 22 is sufficiently high to perform a normal wireless communication. Generally, the wireless radio wave intensity attenuates as it goes away from the access points 22, and therefore, the effective wireless communication range of the access point 22 denotes a range within a specific distance from the access point 22.

The movement measuring component 31 measures a movement amount of the device main body 2 according to an instruction by the controller 5 and outputs it to the controller 5. The controller 5 transfers the movement amount output by the movement measuring component 31 to the information protection component 9. The controller 5 instructs the movement measuring component 31 to measure a movement amount except when the medical measuring device 30 is turned off. It is also preferable to measure a movement amount while the medical measuring device 30 is in a sleep mode.

The information protection component 9 determines whether or not the device main body 2 is in a state being carried, based on the temporal variations in the movement amount, which is output by the movement measuring component 31, or its regularity. Here, the state that the medical measuring device 30 is being carried is determined by a movement between the outside and the inside of the effective wireless communication range of the access point 22. For example, it means a movement between hospital rooms along a corridor of a hospital ward, or a movement between hospital wards. The state that the medical measuring device 30 is being carried has various patterns. As a part of it, various conditions are possible. For example, there is a case that a nurse walks around carryings the device main body 2 in his/her hand. As another example, there is a case that a nurse walks around carrying the device main body 2 by dangling it from his/her neck with a strap, etc. As still another example, there is a case that a nurse walks around carrying the device main body 2 in his/her pocket. As still another example, there is a case that a nurse walks around carrying the device main body 2 in a carrying case held by his/her hand. As still another example, there is a case that a nurse walks around wheeling a cart on which the device main body 2 or a carrying case holding the device main body 2 is loaded. Although it is not preferable, there is also a case that a nurse carries the device main body 2 while running in the aforementioned conditions.

In the respective conditions that the medical measuring device 30 is carried, the output of the movement measuring component 31 indicates different values. However, the outputs of the movement measuring component 31 have, in common, the regularity (periodicity) of an output change of the movement measuring component 31 in a state that the medical measuring device 30 is carried. When the medical measuring device 30 having a predetermined regularity is carried, an output value in at least one axis among the movement amounts of the movement measuring component 31 periodically repeats the same change. On the other hand, in a state that the medical measuring device 30 is not carried, the movement of the medical measuring device 30 is defined as a short movement in a hospital room or a measurement. This movement is not the one that repeats the regularity of the movement amounts as described above, and it is the one that changes a value in any one of the axes irregularly.

The information protection component 9 monitors a value of each axis of a movement amount output by the movement measuring component 31, and determines whether or not a change having he aforementioned regularity occurs periodically. For example, the information protection component 9 compares an output value of the movement measuring component 31 with a threshold value, and determines that the medical measuring device 30 is carried if the output value exceeds the threshold value periodically. In a case that a predetermined time is elapsed from the point of time that a communication component 7 was disconnected with the access point 22 while the state that the medical measuring device 30 is being carried is continued, the information protection component 9 outputs a disclosure regulation signal to the controller 5. On the other hand, even when the wireless communication between the communication component 7 and the access point 22 is temporary disconnected while the medical measuring device 30 is bine carried, in a case that the wireless communication between the communication component 7 and the access points 22 is reconnected, a disclosure regulation signal is not transferred from the information protection component 9 to the controller 5.

A condition that a predetermined time is elapsed from the point of time that the communication component 7 and the access point 22 were disconnected while the carrying condition is continued means that the medical measuring device 30 is moved away more than or equal to a specific distance from the effective wireless communication range of the access point 22*n*. Therefore, it is desired to set a necessary time, for example, for the nurse to take to slowly walk a specific distance out of a hospital. The operations after the disclosure regulation signal has been output from the information protection component 9 to the controller 5 are performed in the same manner as the first embodiment.

As described above, according to the medical measuring device 30 as shown in the second embodiment, even when an arrangement of a wireless communication in a facility where the protection of the personal information data is in a favorable situation is not sufficient, and there is an area Where a wireless radio wave does not reach the medical measuring device 30, the personal information data is not prohibited from being read out unnecessarily. That is, the medical measuring device 30 prohibits the readout of the personal information data only when the medical measuring device 30 is likely to be taken outside a facility such as a hospital, etc. Accordingly, the medical measuring device 30 can suppress deterioration in user-friendliness and improve the protection performance of the personal information data appropriately.

(Third Embodiment)

The medical measuring device 30 in the third embodiment of the present invention performs still another determination processing to prohibit the readout of the personal information data using the information protection component 9. FIG. 5 shows a configuration of the medical measuring device 30 in the present embodiment. In the present embodiment, the information protection component 9 receives a reception radio wave intensity from the communication component 7. The protection component 9 estimates a distance that the medical measuring device 30 is carried as shown in the second embodiment based on the reception radio wave intensity. Therefore, a radio wave reception intensity measuring component 7*a* is provided inside the communication component 7 of the medical measuring device 30 shown in the second embodiment.

First, a relationship between an amount of changes in the reception radio wave intensity and a moving distance of the medical measuring device 30 within the wireless effective range of the access points 22 is preliminarily obtained. This is computed according to experiences such as experiments, and it is stored as moving distance information in the device information area of the recording component 8. The moving distance information is information that associates the changes of the reception radio wave intensity measured by the radio wave reception intensity measuring component 7*a* with the moving distance of the medical measuring device 30. For example, the recording component 8 stores in look-up table the amount of changes of the reception radio wave intensity per unit of time and the moving distance of the medical measuring device 30 corresponding to the respective amount of changes.

The radio wave reception intensity measuring component 7*a* in the communication component 7 measures and outputs the intensity of the reception radio wave in the wireless communication. The radio wave reception intensity measuring component 7*a* may always measure the reception radio wave intensity while the communication component 7 performs a wireless communication. Alternatively, the radio wave reception intensity measuring component 7*a* may perform a measurement of the reception radio wave intensity periodically such as every few seconds or every few minutes. The reception radio wave intensity output by the radio wave reception intensity measuring component 7*a* is the intensity of the radio wave that has reached an antenna (not shown in the drawing) provided in the communication component 7, and the intensity that is attenuated depending on a distance from a radio wave source and ambient environment is measured by using a well-known technique.

The information protection component 9 always computes the amount of changes per unit time of the reception radio wave intensity, which is received from the communication component 7 on an as needed basis. The amount of changes of the reception radio wave intensity is smoothened. by the information protection component 9 so that an approximate amount of changes of the approximate reception radio wave intensity is obtained. The information protection component 9 computes a moving distance corresponding to the approximate amount of changes of the reception radio wave intensity by reading the moving distance information stored in the recording component 8. The information protection component 9 computes an approximate moving speed of the medical measuring device 30 by the moving distance information and the unit of time and stores it. The information protection component 9 keeps updating the moving speed of the medical measuring device 30 every smoothing cycle (unit of time).

In parallel with the aforementioned processing, the information protection component 9 makes a determination of which the medical measuring device 30 is being carried based on the movement amount output by the movement measuring component 31 as shown in the second embodiment. In addition to, or instead of the determination based on the movement amount, the information protection component 9 may make a determination whether or not the medical measuring device 30 is being carried based on the changes of the reception radio wave intensity. For example, when the reception radio wave intensity received from the communication component 7 is monotonously increased or is monotonously reduced for a predetermined period, it may be determined that the medical measuring device 30 shifts in position, or the medical measuring device 30 is being carried.

Under the condition where it is determined that the medical measuring device 30 is being carried, when it is notified that a wireless communication between the communication component 7 and the access point 22 has been disconnected, the information protection component 9 presumes that the medical measuring device 30 is carried out from the effective wireless communication range of the access point 22. In accordance with this, the information protection component 9 starts a count by a timer counter starting from zero. This is to measure an elapsed time since when the wireless communication between the access point 22 and the communication component 7 was discussed. A predetermined distance, which was preliminarily defined, is divided by an approximate moving speed of the medical measuring device 30 stored at the point of time that the wireless communication between the access point 22 and the communication component 7 was disconnected, and its result is obtained as a window time.

The predetermined distance is a distance of an acceptable area, where the medical measuring device 30 is likely to be in a favorable situation in view of the data protection of the medical measuring device 30 even though it is outside of the effective wireless communication range of the access point 22, from a boundary of the effective wireless communication. The obtained window time is a necessary time for the communication measuring device 30 to move farther than the aforementioned predetermined distance from the boundary of the effective wireless communication range on the assumption that the medical measuring device 30 keeps moving at the approximate moving speed of the medical measuring device 30 at the time that the wireless communication was disconnected. That is, the window time is the time that is necessary for the medical measuring device 30 to move the distance between the effective wireless communication range of the access point 22 and a position where the readout of the personal information data should be prohibited.

When the count value of the timer counter reaches the aforementioned window time, the information protection component 9 determines whether or not the carrying of the medical measuring device 30 has been continued since the count of the timer counter was started. It includes a case that the carrying of the medical measuring device 30 is still ongoing. That is, the information protection component 9 continues the determination of the carrying based on the movement amount of the medical measuring device 30 even after the count of the tinier counter is started. When the periodic changes with the aforementioned regularity occur sequentially or continuously, the information protection component 9 determines that the carrying of the medical measuring device 30 is ongoing so that a disclosure regulation signal is output.

On the other hand, there is a case that the periodic changes with the regularity is stopped before the window time elapses, and after that, the information protection component 9 does not detect the movement amount to determine the carrying of the medical measuring device 30. In this case, it determines that the carrying is completed within the acceptable area where the device is in a favorable situation though it is outside of the effective wireless communication range of the access point 22 and that the medical measuring device 30 is located in an effective range, in which case the information protection component 9 does not output a disclosure regulation signal.

However, only in the case that the readout of the personal information data is allowed, and after that, if the movement amount that makes a determination of carrying the medical measuring device 30 is detected again, the information protection component 9 outputs a disclosure regulation signal until a wireless communication with the access point 22 is effectively established again. That is, after the readout of the personal information data has been prohibited, the information protection component 9 allows the personal information data to be read out when a wireless communication by the communication component 7 is established again.

According to the aforementioned medical measuring device 30 of the present embodiment, even when the arrangement of the wireless communication is not sufficient and there is an area where the wireless radio wave does not reach even within a facility, the deterioration in user-friendliness of the medical measuring device 30 is appropriately suppressed and it is possible to improve the protection performance of the personal information data.

(Fourth Embodiment)

Figure 6:
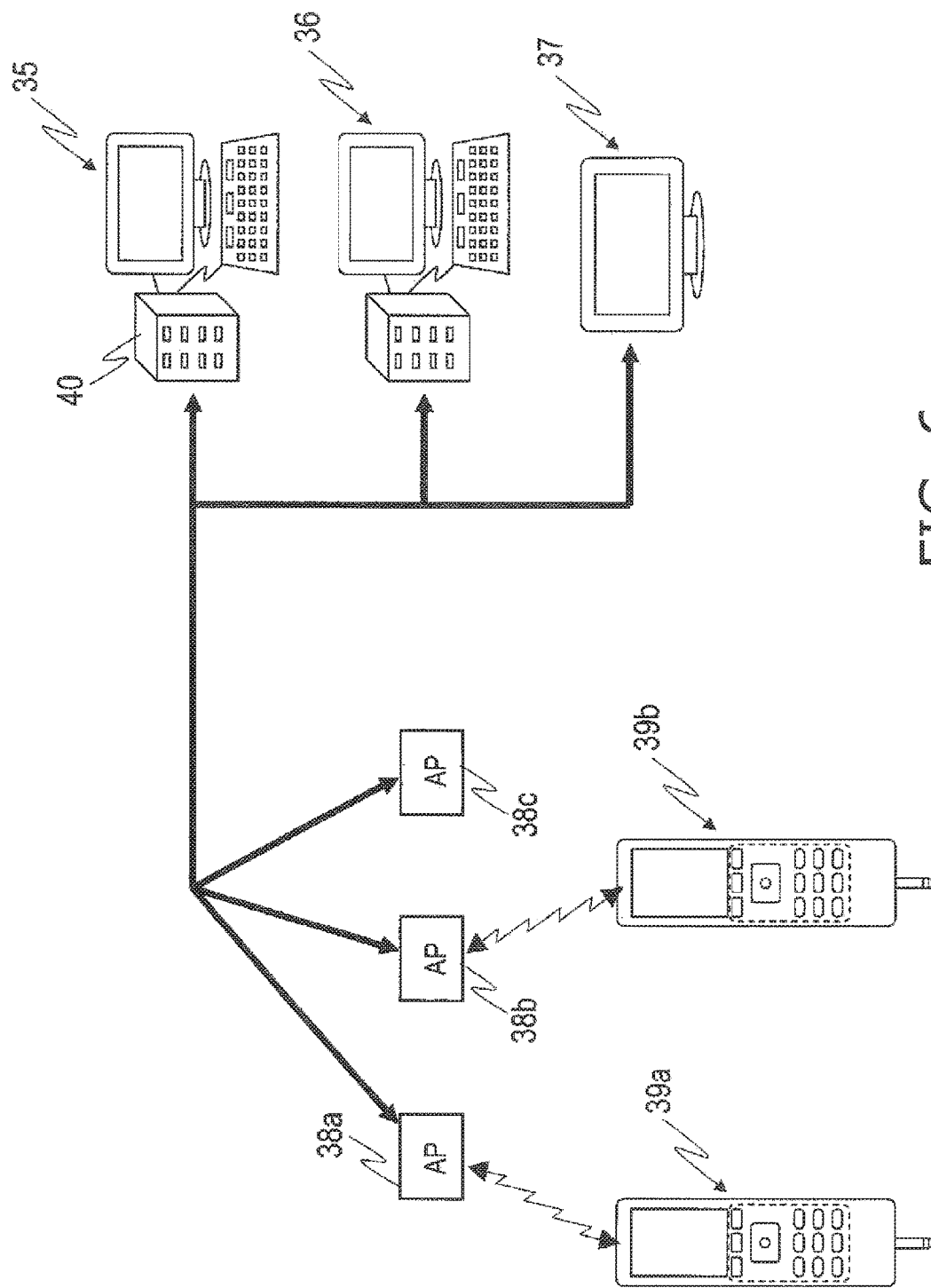
FIG. 6 is a schematic diagram showing a configuration of a medical measuring system in the fourth embodiment.

The fourth embodiment is a medical measuring system comprising the medical measuring devices 1, 30 described in the first to third embodiments above, and a management device that manages these devices and protects the personal information data stored in the system. FIG. 6 is a schematic diagram showing a configuration of a medical measuring system. The medical measuring system is configured by a main server 35, a secondary server 36, and an information monitor 37, a plurality of access points 38a to 38c, and a plurality of medical measuring devices 39a, 39b. The secondary server 36 and the information monitor 37 are connected to the main server 35 through intranet. The access points 38a to 38c are provided on intranet to form a wireless network. The medical measuring devices 39a, 39b are wirelessly connected to any one of the access points 38a to 38c. In the present embodiment, an example that a server information protection component 40 is provided in the main server 35 to protect the personal information data used in the system is described. In the present embodiment, the main server 35, the secondary server 36, and the information monitor 37 functions as a management device of the medical measuring devices 39a, 39b.

The main server 35, the secondary server 36, and the information monitor 37 are installed in a facility of a hospital, etc. The main server 35, the secondary server 36, and the information monitor 37 mainly manages the personal information data of patients such as an electronic medical record. The medical measuring devices 39a, 39b collect measurement managing data of the patients, and display them if necessary for treatments, or as required by nurses, etc. For example, the main server 35 records and manages a database of personal information data of all patients who at least stay inside facility or use the facility. Alternatively, under the management of the main server 35, the database of the personal information data may be divided for each category, and it may be distributed and recorded to a plurality of terminals.

Further, the main server 35 grasps and manages locations and operating conditions of all of the medical measuring devices 39a, 39b that operate inside facility.

The secondary server 36 is arranged in, for example, an examination room, a laboratory room, or a nurse station. The secondary server 36 receives an input of necessary information by medical workers. Further, the secondary server 36 displays the contents for instructing the main server 35 directed to the medical workers.

The information monitor 37 is installed in a nurse station, etc. The information monitor 37 displays information of patients or information on a facility according to an instruction of the main server 35 or the secondary server 36. According to the medical measuring system, an example that the plurality of servers 35, 36 and the information monitor 37 which are used in a role of a management device is disclosed, but depending on the size of a facility, the management device may be configured by one server, or more number of servers and information monitors.

The main server 35 has a database which registers all of information of the medical measuring devices 39a, 39b. The main server 35 reciprocally communicates with the medical measuring devices 39a, 39b and monitors their operation conditions while both of the medical measuring devices 39a, 39b are turned ON and they are in operation. When the readout of the personal information data is requested from the medical measuring devices 39a, 39b registered in the database, the server information protection component 40 determines whether or not it is allowed.

For example, there is a case that the medical measuring device 39a is taken out from a facility and is connected to the Internet outside of the facility, and the medical measuring device 39a is connected to the main server 35 by some means. In this case, the server information protection component 40 acquires addresses of access points which are relaying the communication, etc., and a communication path to the medical measuring device 39a is checked. Accordingly, the server information protection component 40 is informed that the medical measuring device 39a does not perform a communication through any of the access points 38a to 38c in the facility. Because of this, the server information protection component 40 determines that the access from the medical measuring device 39a is an unauthorized access. An access request from the medical measuring device 39a is then refused and the readout of the personal information data is not permitted.

Further, the server information protection component 40 monitors whether or not the medical measuring devices 39a, 39b are improperly disconnected from the wireless network in the facility. Specifically, when the communication was suddenly disconnected without a reception of a notification that the power has been turned off in a normal manner from the medical measuring devices 39a, 39b, which were normally operated and were reciprocally communicated in a facility of a hospital, etc., the server information protection component 40 orders the main server 35 to present an alarm display. Further, the server information protection component 40 may also order an alarm display to be presented at the secondary server 36 and the information monitor 37, which take a role of a management device, and other medical measuring devices which are connected by a wireless communication.

The contents of the alarm display include an unique identification number such as a management number of the medical measuring device 39, a nickname associated with the medical measuring device, a place such as a department, etc. where the medical measuring device is managed and is daily used, locations of access points 38 where the last communication was performed when the communication was disconnected. By displaying these pieces of information, it urges the medical workers to identify a location of the medical measuring device 39 that the communication is disconnected. Further, at this time, the server information protection component 40 prohibits the readout of the personal information data stored in the main server 35 according to a request from the disconnected medical measuring device 39 until the input for which the location of the medical measuring device 39 has been identified is made to the main server 35 by the medical workers. The location identification of the medical measuring device 39 may be inputted to the secondary server 36 or another wirelessly connected medical measuring device by the medical workers. In this case, the inputs made by the medical workers may be forwarded from the secondary server 36 or another medical measuring device to the main server 35 and are then informed to the server information protection component 40.

Accordingly, the server information protection component 40 identifies the medical measuring device 39 which is missing because the medical measuring device 39 has been taken out, etc. Even when an unauthorized access was attempted by the medical measuring device that has been taken out, it is possible to prevent the personal information data from leaking.

Further, the server information protection component 40 may store map information of inside the building of a facility and may track the movements of the medical measuring devices 39a, 39b. By receiving a reception radio wave intensity and a movement amount from the medical measuring devices 39a, 39b occasionally, the server information protection component 40 can identify approximate locations of the medical measuring devices 39a, 39b based on the access point 38, which relays the communication, as a starting point. By the tracking using the map, when the medical measuring devices 39a, 39b is taken out from the facility, a request of an unauthorized access can be rejected.

As described above, according to the medical measuring system of the present embodiment, it is possible to prevent the personal information data stored in the facility from being illegally read out by a third person when the medical measuring device 39 is taken out.

(Fifth Embodiment)

Figure 7:
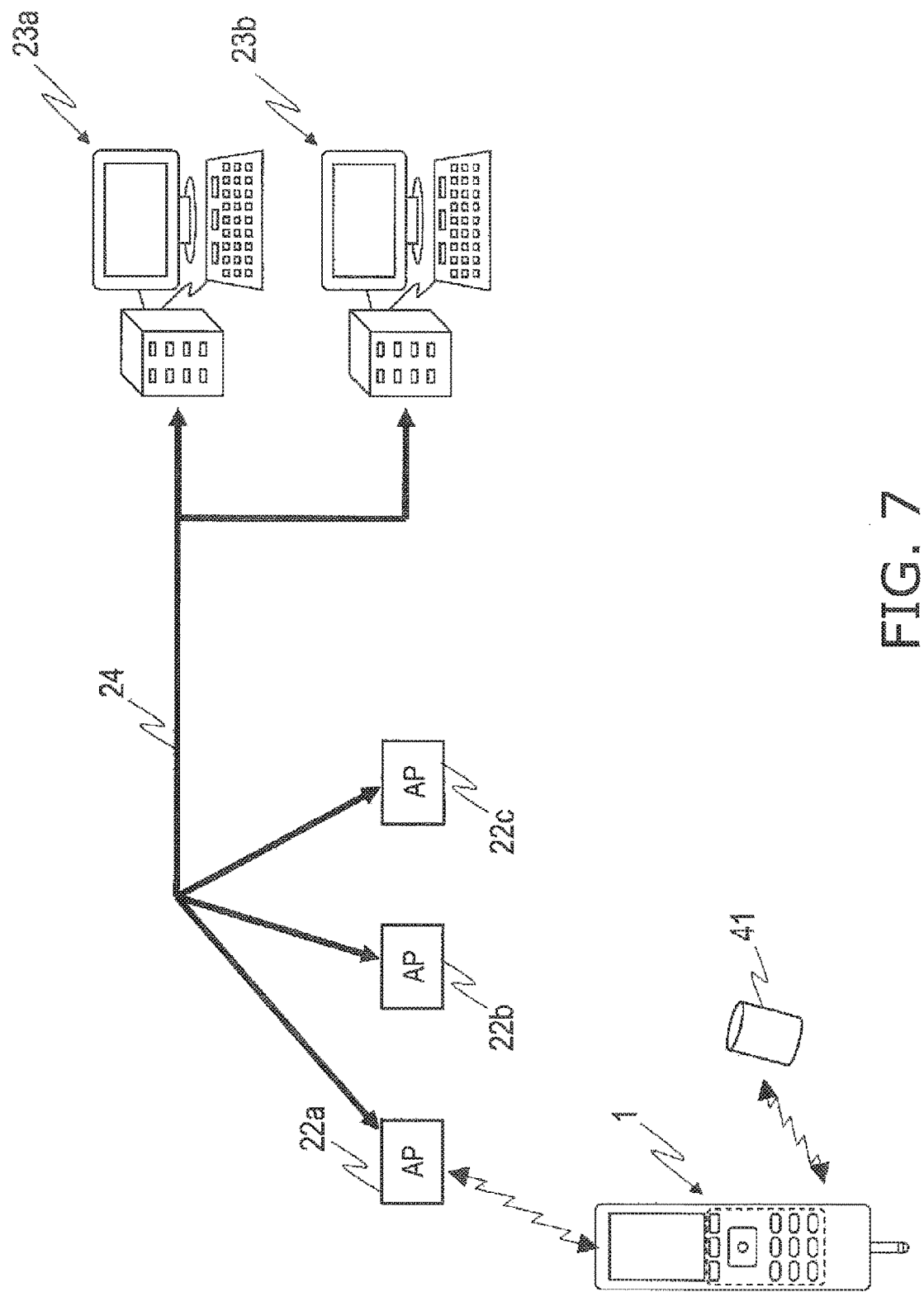
FIG. 7 is a schematic diagram showing a configuration of a medical measuring device and its peripheral devices in the fifth embodiment.
Figure 8:
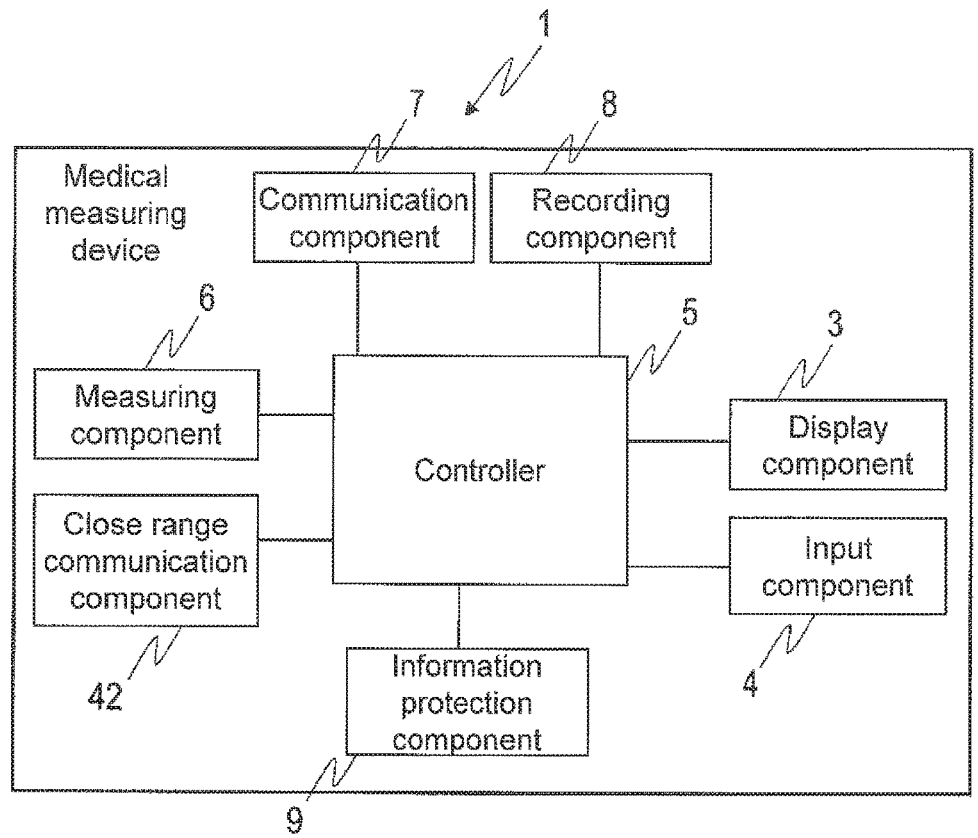
FIG. 8 is a block diagram showing a configuration of a medical measuring device in the fifth embodiment.

FIG. 7 and FIG. 8 are diagrams showing a configuration of a medical measuring system that includes a medical measuring device 1 and its peripheral devices in the present embodiment. FIG. 7 is a schematic diagram showing a connection between the medical measuring device 1 and its peripheral devices. FIG. 8 is a functional block diagram of the medical measuring device.

As shown in FIG. 7, the medical measuring system includes an administration key 41 as a peripheral device of the medical measuring device 1. As shown in FIG. 8, in the medical measuring device 1, the administration key 41 and a close range communication component 42 to perform the Near Field Communication are provided. In the disclosure of the present embodiment, some configurations and operations other than the close range communication component 42 of the medical measuring device 1 are not disclosed and these components are omitted because they are the same as the first embodiment.

First, the administration key 41 will be explained. The administration key 41 transmits a permission signal to the medical measuring device 1. The information protection component 9 of the medical measuring device 1 makes a determination whether the medical measuring device 1 is in "a favorable situation" or in "an unfavorable situation" depending on the permission signal of the administration key 41.

Figure 9:
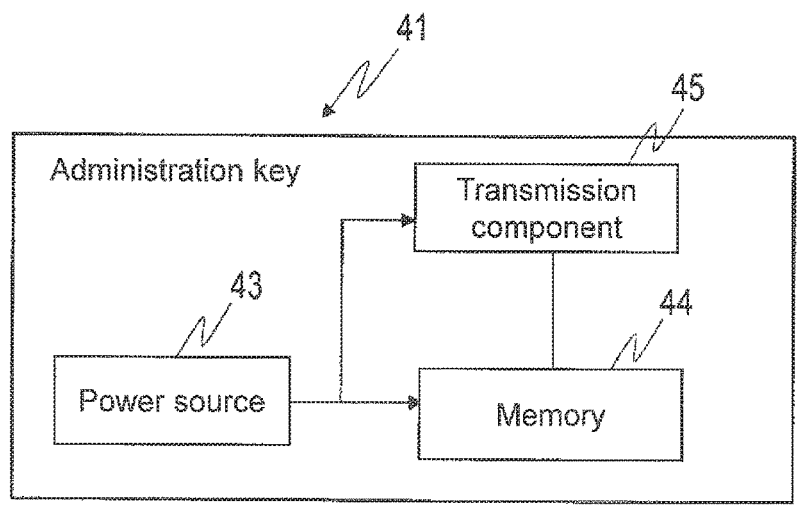
FIG. 9 is a block diagram showing a configuration of an administration key.

FIG. 9 shows a block diagram showing a configuration of the administration key 41. The administration key 41 is provided with at least a power source 43, a memory 44, and a transmission component 45. The power source 43 supplies drive power to the memory 44 and the transmission component 45. The administration key 41 is a portable device to be carried so that the power source 43 is configured by a disposable primary battery cell or a chargeable secondary battery cell. When using the secondary battery cell, the secondary battery cell may be detached and charged by an external charger. Alternatively, a charge circuit (not shown in the drawing) may be further provided in the power source 43 and the secondary battery cell in a state of being mounted on the administration key 41 may be charged.

A device ID uniquely assigned to the administration key 41 is stored in the memory 44. The device ID is a character string, a number string, or the combination of these strings uniquely assigned to each administration key 41 when the administration key 41 is produced or when it is delivered to the user. Alternatively, the device ID may be a common ID shared in a group composed of a plurality of administration keys 41. In this case, the plurality of administration keys 41 having the same device ID is distributed to a plurality of users in a facility.

The transmission component 45 is provided with an antenna (not shown in the drawing) The transmission component 45 reads the device ID stored in the memory 44 and performs a modulation such as an error correction, etc., and after changing the ID into an appropriate format for a wireless communication, the transmission component 45 wirelessly transmits the m through the antenna. The transmission by the transmission component 45 is intermittently repeated every several seconds or several tens of seconds. The wireless signal transmitted by the transmission component 45 becomes a permission signal for the medical measuring device 1.

The wireless signal that the transmission component 45 transmits is a wireless radio wave for the Near Field Communication, and the effective communication range is preferably from several tens centimeters to several meters. This is to keep the permission signal workable only when the administration key 41 and the medical measuring device 1 are located near each other in a limited space such as at least in the same room, etc.

Next, the medical measuring device 1 in the present embodiment will be explained. The close range communication component 42 receives the wireless radio wave of the permission signal that the aforementioned administration key 41 transmits. When the radio wave transmitted by the administration key 41 is received by an antenna (not shown in the drawing), the close range communication component 42 performs a demodulation such as an error correction, etc. and performs an extraction of the device ID of the administration key 41. The close range communication component 42 makes a determination whether a radio wave of the close range communication is received or not and then a determination for existence or non-existence of a device ID if the radio wave has been received. When extracting the device ID, the close range communication component 42 outputs the extracted device ID to the information protection component 9. An antenna may be provided in the close range communication component 42. Or, if the antenna provided in the communication component 7 can receive the close range communication, the antenna may be used for both.

The information protection component 9 performs an authentication of the received device ID output by the close range communication component 42 at a specific timing. Based on the result, the information protection component 9 determines whether or not to output a disclosure regulation signal to the controller 5. It is possible to arbitrarily set the specific timing. For example, it is possible to set the specific timing when the medical measuring device 1 is turned on. As another example, it is possible to set the specific timing when a user starts inputting the user ID, etc. by operating the input component 4 in order to perform a measurement. As another example, it is possible to set the specific timing when a user operates the input component 4 so that the personal information data stored in the recording component 8 is read out in order for the user to review the measurement result. Alternatively, it is not limited to the specific timing, but the aforementioned determination may be made at regular intervals at any time other than the time that the medical measuring device 1 is turned off.

The information protection component 9 determines whether the device ID of the administration key 41 extracted from the wireless signal received by the close range communication component 42 corresponds to the device m preliminarily stored in the recording component 8. When the received device ID of the administration key 41 corresponded to the device m stored in the recording component 8, the information protection component 9 does not output a disclosure regulation signal because a permission signal by the administration key 41 is valid. The information protection component 9 determines whether the permission signal from the administration key 41 is valid regardless of a connection status of the wireless communication with the access point 22 by the communication component 7. Alternatively, the information protection component 9 may determine whether the permission signal from the administration key 41 is valid only when the communication component 7 connects with the access point 22 in a wireless communication. In the former case, regardless of whether the medical measuring device 1 is located within the effective wireless communication range of the access point 22, as far as the administration key 41 is carried with the medical measuring device 1, it is determined that the device is in "a favorable situation". In the latter case, only when the medical measuring device 1 is located within the effective wireless communication range of the access point 22 and the administration key 41 is carried with the medical measuring device 1, determined that the device is in a "favorable situation".

On the other hand, regardless of the connection state of the wireless communication with the access point 22 by the communication component 7, when the permission signal from the administration key 41 is not valid, the information protection component 9 outputs a disclosure regulation signal to the controller 5. For example, the case that the permission signal from the administration key 41 is not valid corresponds to a case that a wireless signal transmitted by the administration key 41 is not received by the close range communication component 42. As another example, the case that the permission signal from the administration key 41 is not valid corresponds to a case that a device ID of any of the administration keys 41 is not extracted from the wireless signal received by the close range communication component 42. Still, as another example, the case that the permission signal from the administration key 41 is not valid corresponds to a case that the received device ID does not correspond to the device ID preliminarily stored in the recording component 8.

Here, when the medical measuring device 1 is installed a facility, the device ID of the administration key 41 used as a pair is stored in the recording component 8. At this point, the device ID's of the plurality of administration keys 41 may be stored. In this case, when the extracted device m corresponds to any one of the plurality of device ID's preliminarily stored in the recording component 8, the information protection component 9 determines that the permission signal from the administration key 41 is valid.

The controller 5 controls to permit or prohibit the readout of the personal information data stored in the recording component 8 based on a determination whether or not a disclosure regulation signal is output from the information protection component 9 in the same manner as described in the first embodiment. However, only when a disclosure regulation signal is output from the information protection component 9 while the measurement operation of the biological information is performed by the measuring component 6, the controller 5 invalidates the disclosure regulation signal until the measurement operation is completed.

Therefore, in the medical measuring system of the present embodiment, in the state that a specific one or the plurality of administration keys 41 and the medical measuring device 1 associated with it are located near each other, it is determined that the medical measuring device 1 is in a favorable situation for the data protection of the medical measuring device 1. On the other hand, when the administration key 41 is not located near the medical measuring device 1, it is determined that the medical measuring device 1 is not in a favorable situation for the data protection of the medical measuring device 1.

That is, in such a state that the user, who is permitted to read out the personal information data by a facility, carries the administration key 41, only when the user controls the medical measuring device 1 associated with the administration key 41 or another person controls it in the state the user attends him/her, the medical measuring device 1 is permitted to freely read out the personal information data. In other words, an authentication is made by using the administration key 41.

Therefore, the users who are authorized by a facility are allowed to read out the personal information data in the medical measuring device 1. Because of this, regardless of whether or not the medical measuring device 1 is taken out from a facility, when the medical measuring device 1 is illegally accessed by a third person who is not permitted by the facility, the protection performance of the personal information data can be improved.

The administration key 41 can be provided as a very small and low-cost device. Therefore, if the administration key 41 is lent to every one of the users, it is easy for the user to carry it at any time by wearing it on a neck strap, a wristband, etc.

Further, the administration keys 41 may be unified with a name plate or a security key that is used for a personal authentication in the facility, and if its storage management is strictly carried out, the security can be further improved. In this case, it is possible for the user to read out the personal information data of the medical measuring device 1 by carrying the administration key 41, and as a result, the deterioration in user-friendliness is suppressed and the protection performance can be improved.

The device ID associated with the administration key 41 may be paired with the ID of a user carrying the administration key 41 and preliminarily stored in the recording component 8 of the medical measuring device 1. The controller 5 performs an authentication by using the device ID of the administration key 41, and when the normal measurement of glucose concentration is permitted, the user ID stored as a pair of the device ID of the authenticated administration key 41 is read from the recording component 8. Accordingly, the controller 5 interrelates the ID of the user, who performs the measurement, with the measurement result. As a result, the input of the user ID when the measurement of glucose concentration is performed as described in the first embodiment can be omitted. Further, the controller 5 controls the display component 3 to display the user ID or the user name related to it so that it may be confirmed.

The information protection component 9 may record a history of authentication for the device ID's of the administration keys 41 with time in the recording component 8. The controller 5 may then transmit the history to the servers 23a, 23b through the communication component 7 periodically, for example, once a day, etc. Therefore, based on the history transmitted from the medical measuring device 1, the state of use of the medical measuring device 1 or the state of operations done by the user who carries the administration key 41 can be managed and supervised in the servers 23a, 23b.

Further, the administration key 41 may be provided with a display component and a reception component. The administration key 41 performs a reciprocal communication with the medical measuring device 1, and the authentication result of the device ID of the administration key 41 by the medical measuring device 1, etc. may be displayed on the display component of the administration key 41. At this point, the administration key 41 and the medical measuring device 1 are connected by a close range wireless communication method such as a BLUETOOTH (registered trademark) or the RF-ID, etc. so that a transmission and a reception of the information are performed.

The administration key 41 may be further provided with a button as an input means, When the user pushes the button of the administration key 41, the medical measuring device 1 associated with the administration key 41 may light up the display component of itself or a lamp, or may generate an alarm sound from a sound generation component. For this purpose, the administration key 41 transmits a command response signal with a device m from the transmission component 45 when the user pushes a button. The medical measuring device 1, which has received the device ID transmitted by the administration key 41, determines whether the command response is included in the received signal at the same time when it authenticates a relation of the received device ID to the medical measuring device 1 itself When the command response is included, the medical measuring device 1 performs operations to alert the surroundings for indicating its own existence to by using the display component, the lamp, or the sound generation component.

However, when the medical measuring device 1 is used by the user at the time of measuring, etc., a communication operation in response to the command response is kept invalid.

Therefore, it is possible to easily specify the location of the medical measuring device 1 associated with the administration key 41. This is useful, for example, when the user wants to find out the medical measuring device 1 associated with the administration key 41 carried by him/her in the state that multiple medical measuring devices 1 are managed and stored in the same room such as a nurse station in a hospital ward, etc. Further, for example, it is useful when the medical measuring device 1 is missing for such a reason that it is hidden under bed sheets, clothes, etc.

As one configuration of the administration key 41, it may have a configuration of a docking station of the medical measuring device 1. This is a base on which the medical measuring device 1 is mounted, and it is sometimes called as a cradle. For example, in such a state of use that the user mounts the docking station on a wagon and goes round with it, both the medical measuring device 1 and the docking station are carried together so that the function as the administration key can be achieved.

Alternatively, the administration key 41 may be configured as a part of the docking station of the medical measuring device 1, in which case the administration key 41 may be separated from the docking station when being carried.

The example that the electrochemical type biosensor 10 is mounted on the medical measuring device 1, and the blood of the biological object is deposited as a liquid sample, and the glucose concentration in the blood is measured was explained above, but this is not an only option in all the embodiments.

As a liquid sample, liquid concentrate or liquid solution of a sample that can be obtained from a biological object such as blood, urine, interstitial fluid, etc. can be used. Alternatively, it may be a pseudo product or an experimental product of these samples. Further, a process solution that has been pre-treated such denaturation, chemical modification, etc. may be used. Alternatively, when a control liquid, etc. for a purpose of calibration of the measuring device is used, the present invention is applicable.

As an object to be measured, the present invention is applicable for what are subject to expression or quantitative estimation in a sample, such as sugars, lactic acids, various cholesterols, nucleic acids, DNA, antibodies, antigens, proteins, hormones, bacteria, enzymes, drugs, antibiotics, pharmaceutical compositions, markers, chemical substances, etc.

As the biosensor 10, such a configuration is applied that the deposited liquid sample is spread by an act of a flow channel, a membrane, etc. or a chamber, etc. is provided for retaining the deposited liquid sample. Alternatively, a biochip or a DNA chip that executes a preprocessing such as hybridization, blood cell contraction, blood cell destruction, etc. may be used instead of the biosensor 10.

Further, the supply method of the liquid sample to the biosensor 10 is not only the method of depositing it directly from a biological object, but also a method of supplying it through a syringe, a cartridge, preprocessing container, etc. A measurement of an object may be performed in a state that the cartridge or the preprocessing container for supplying a liquid sample is mounted on the biosensor 10.

In addition, the measurement in the medical measuring device 1 includes all possible measurement methods that can be carried out by a handheld measuring device, such as an optical method or a magnetic method.

The medical measuring device 1 mounting the biosensor 10 thereon was explained as an example in the embodiments, but it is not limited to this configuration of the measuring device. It is possible to apply all the handheld devices that are used in an environment in which the measurement results are associated with a lot of personal information in a medical facility, etc. and managed. Such a handheld device includes, for example, an oxygen saturation measuring device, a blood pressure measuring device, an ultrasonic diagnostic device, etc.

The entire contents of Japanese Patent Application No. 2011-283198 (filed on Dec. 26, 2011) is incorporated herein by reference.

INDUSTRIAL APPLICABILITY

The aforementioned medical measuring device is useful as a measuring device, etc. used in a facility, etc. such a hospital where many and unspecified personal information are collected and managed. According to the aforementioned medical measuring device, it is possible to suppress deterioration in its user-friendliness and to improve a protection performance of the personal information data.

What is claimed is:

1. A medical measuring device configured to measure biological information and communicate with a management device by wireless communication, the medical measuring device comprising:

a housing configured to have mounted thereon a biosensor in an attachable and detachable manner, the biosensor being configured to have a liquid sample of a biological object deposited thereon, a measuring component provided in the housing and configured to measure biological information from the liquid sample of the biological object;

a recording component configured to store the biological information measured by the measuring component, to store personal information data, and to store a plurality of user IDs;

an input component configured to receive an inputted user ID;

an information protection component configured to authenticate the inputted user ID at a predetermined time set after the medical measuring device is turned on, to determine that readout of the biological information measured by the measuring component stored in the recording component is to be prohibited when the inputted user ID does not correspond to any of the user IDs stored in the recording component, and to determine that readout of the biological information measured by the measuring component stored in the recording component is not to be prohibited when the inputted user ID corresponds to a user ID stored in the recording component;

a memory storing a program;

a close range communication component configured to perform near field communication with the management device; and a controller programmed to execute the program stored in the memory to:

perform authentication using information obtained from the management device via the close range communication component, control a permission or a prohibition of the readout of the personal information data based on a determination result made by the information protection component, and permit the measurement of the biological information by the measuring component even while the management device is unauthenticated.

2. The medical measuring device according to claim 1, wherein the predetermined time is a time when the inputted user ID is received by the input component.

3. The medical measuring device according to claim 1, further comprising a display component, wherein
the controller is programmed to execute the program stored on the memory to read out a user ID from the recording component and to control the display component to display a user name related to the user ID read out from the recording component.

4. The medical measuring system according to claim 3, wherein
the controller is programmed to execute the program stored on the memory to control the recording component to store the inputted user ID as corresponding with the biological information measured by the measuring component.

* * * * *